US00PP37509P2

(12) United States Plant Patent
Woods

(10) Patent No.: US PP37,509 P2
(45) Date of Patent: Jun. 30, 2026

(54) ***HIBISCUS* PLANT NAMED 'RWOODS11'**

(50) Latin Name: *Hibiscus syriacus*
Varietal Denomination: RWOODS11

(71) Applicant: Spring Meadow Nursery Inc, Grand Haven, MI (US)

(72) Inventor: Roderick Ian Woods, King's Lynn (GB)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 19/370,968

(22) Filed: Oct. 28, 2025

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 5/02
See application file for complete search history.

*Primary Examiner* — Kent L Bell

(57) ABSTRACT

A new and distinct cultivar of *Hibiscus* plant named 'RWOODS11' is disclosed, characterized by large, single, reddish-pink flowers with a darker red central starburst/eye. Flowers open fully to a large, flat disc, with strongly overlapping petals. Plants are vigorous and floriferous, with upright, dense habits. The new cultivar is a *Hibiscus*, typically produced as an outdoor ornamental plant.

4 Drawing Sheets

Latin name of the genus and species: *Hibiscus syriacus*. Cultivar denomination: 'RWOODS11'.

BACKGROUND OF THE INVENTION

The new *Hibiscus* cultivar is a product of a planned breeding program by the inventor to develop new *Hibiscus* cultivars with large flowers in clear colors on vigorous shrubs. *Hibiscus* 'RWOODS11' is the result of the crossing of the seed parent, an unpatented, internally selected *Hibiscus* seedling named '12875', and the pollen parent, an unpatented, internally selected *Hibiscus* seedling named '12911'. The crossing resulting in this new cultivar was made in August 2012 at a nursery in Norfolk, United Kingdom. The new cultivar was found and selected by the inventor in a group of seedlings from the crossing at the same nursery in Norfolk United Kingdom in July 2013.

Asexual reproduction of the new cultivar 'RWOODS11' was first performed in February of 2014 in Norfolk, United Kingdom, by grafting. Subsequent propagation has shown that the unique features of this cultivar are stable and reproduced true to type in successive generations.

SUMMARY OF THE INVENTION

The cultivar 'RWOODS11' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RWOODS11'. These characteristics in combination distinguish 'RWOODS11' as a new and distinct *Hibiscus* cultivar:

1. Large, single, reddish-pink flowers with a darker red central starburst/eye.

2. Flowers that open fully to a large, flat disc, with strongly overlapping petals.
3. Heavily flowering.
4. Vigorous, healthy growth.
5. Upright and dense habit.

PARENT COMPARISONS

Plants of 'RWOODS11' are similar in some horticultural characteristics to the seed parent. The new cultivar, however, differs in the following:

1. Flower color of the new cultivar is a richer and darker color with less blue tones, while the flower color of the seed parent is a lighter color with more blue tones.
2. Flowers of the new cultivar are larger than flowers of the seed parent.

Plants of 'RWOODS11' are similar in some horticultural characteristics to the pollen parent. The new cultivar, however, differs in the following:

1. Flower color of the new cultivar is a richer and darker color with less blue tones, while the flower color of the pollen parent is a lighter color with more blue tones.
2. Flowers of the new cultivar are larger than flowers of the pollen parent.

COMMERCIAL COMPARISON

Plants of 'RWOODS11' are similar in some horticultural characteristics to the cultivar *Hibiscus* 'Minsyrou17', U.S. Plant Pat. No. 33,258. The new cultivar, however, differs in the following:

1. Flower color of the new cultivar is a darker, more vibrant pinkish-red, while the flower color of this comparator is a lighter, less vibrant pinkish-red.
2. Flowers of the new cultivar open more fully; overall flower shape is more flattened and disc-like, while flowers of this comparator open less fully; overall flower shape is less flattened and more concave/cupped.

3. Flowers of the new cultivar are larger than flowers of this comparator.

BRIEF DESCRIPTION OF THE PHOTOGRAPHS

The accompanying photograph in FIG. 1 illustrates in full color a typical plant of 'RWOODS11' grown in a poly-greenhouse in Grand Haven, Michigan. This plant is approximately 3 years old, shown in a 3-gallon container.

Figure 1:
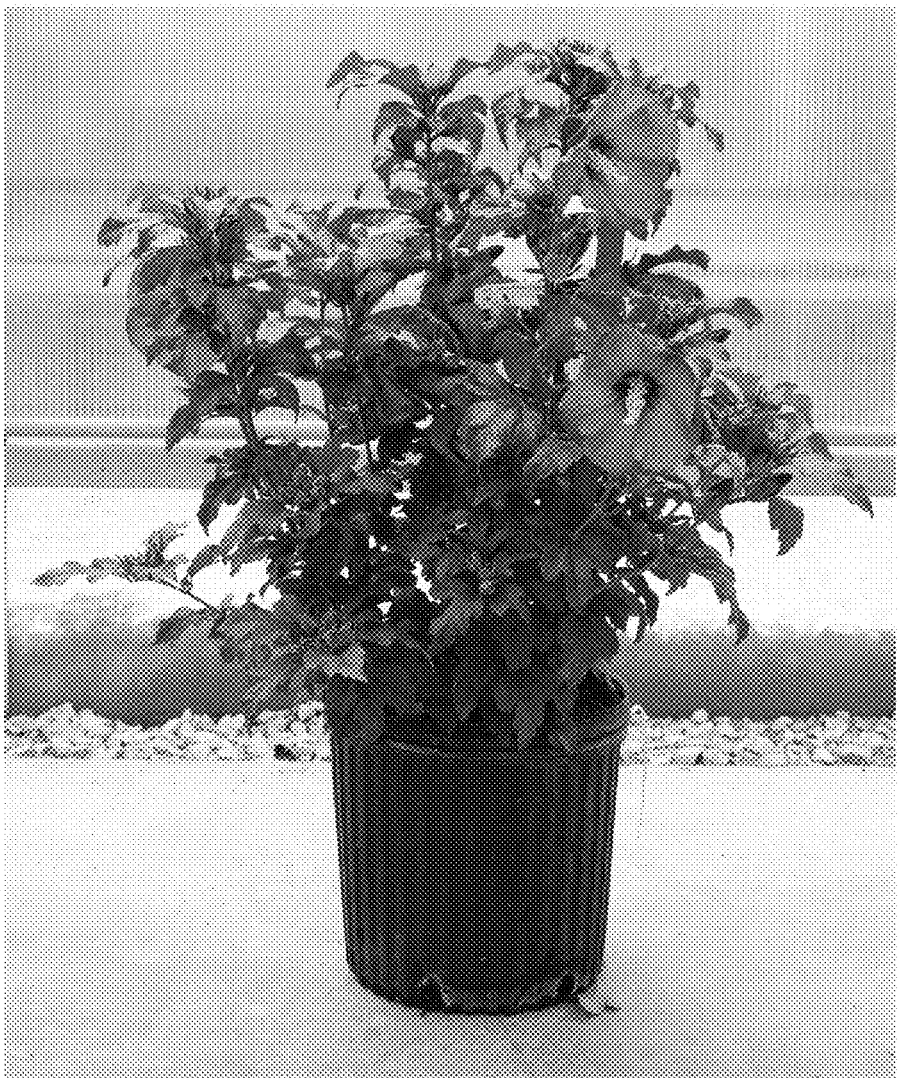
Figure 2:
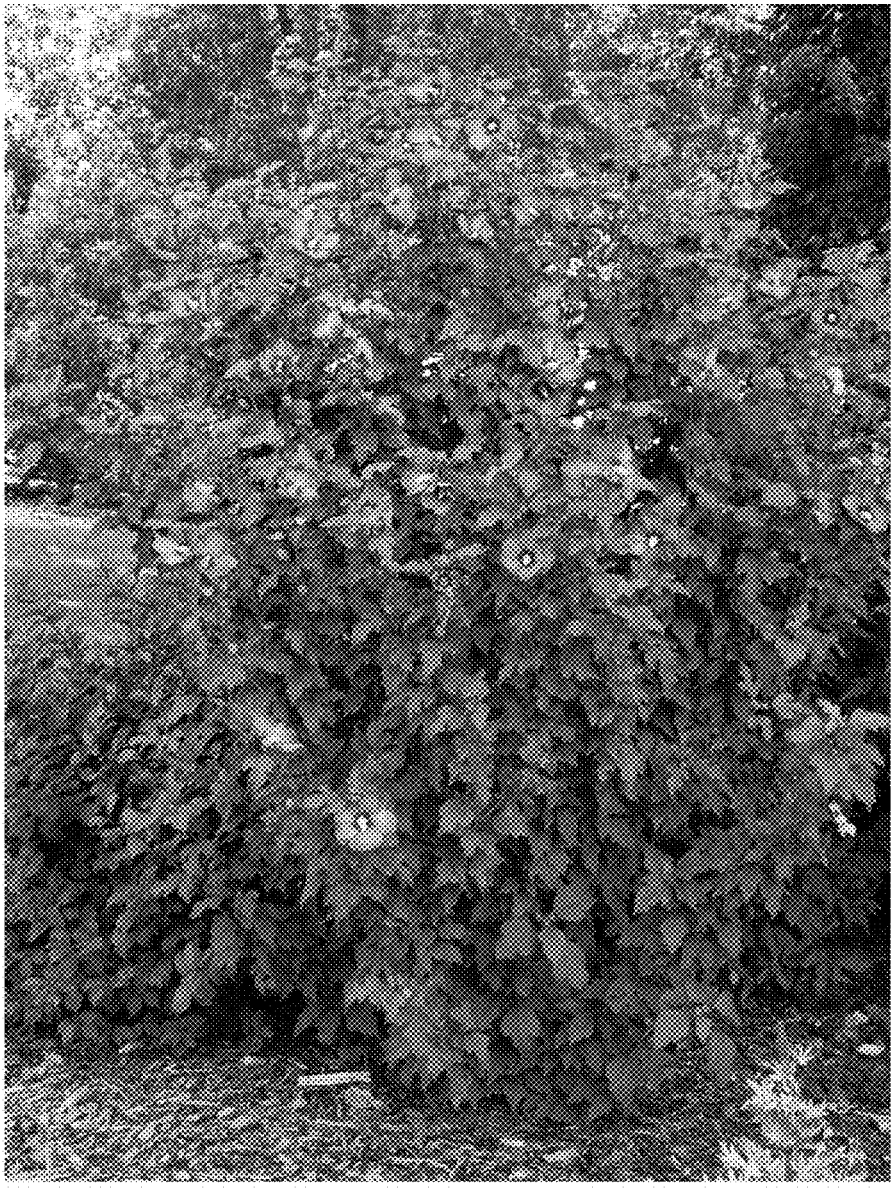
FIG. 2 is a photograph of a mature plant of approximately 5 years old growing outdoors in the ground in Norfolk, UK.
Figure 3:
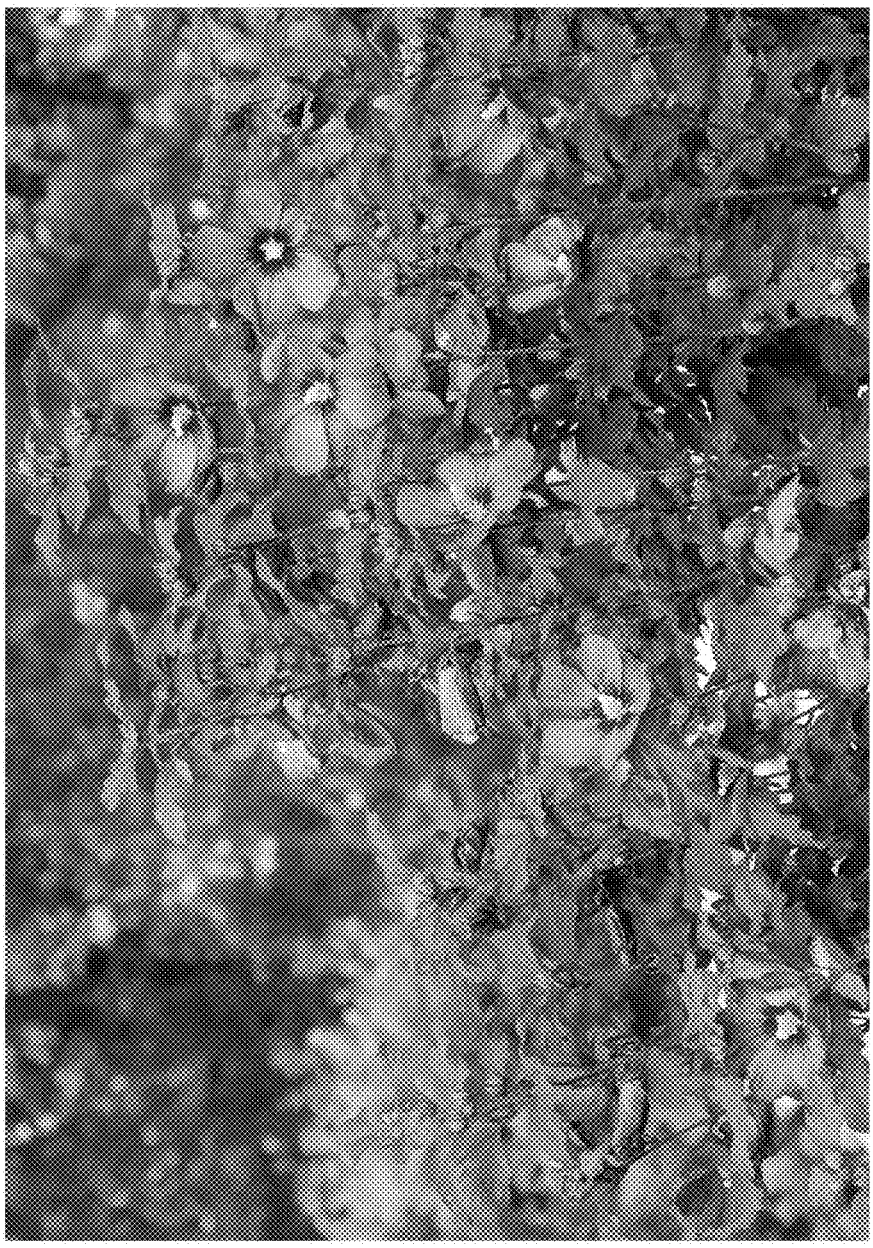
FIG. 3 illustrates a closer view of the foliage and flowers of the plant in FIG. 2.
Figure 4:
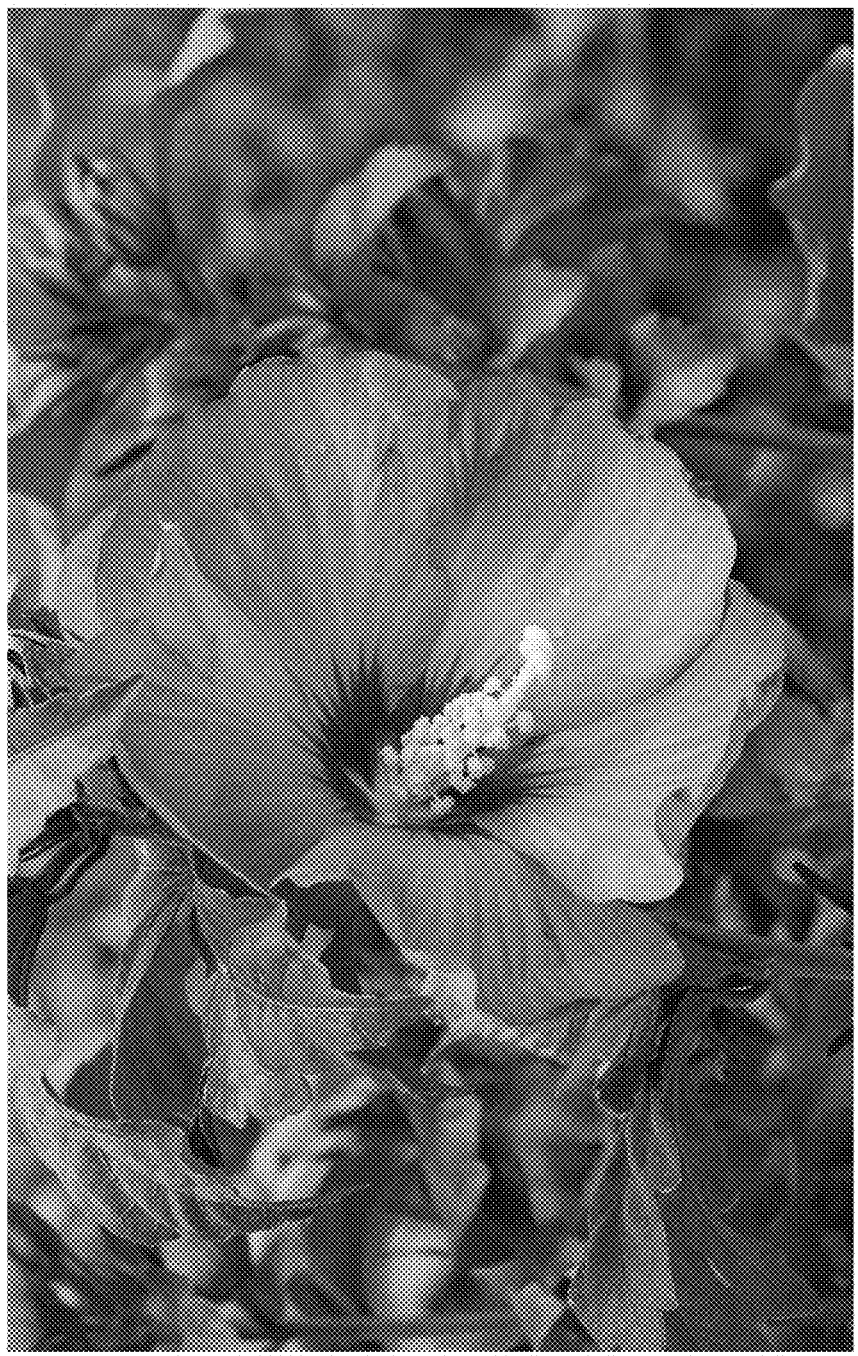
FIG. 4 is a close-up view of an individual flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe a 'RWOODS11' plant. This plant is approximately 3 years old, grown in a #3 container. Temperatures ranged from 18° C. to 27° C. during the day to 5° C. to 10° C. at night. No artificial light, photoperiodic treatments were given to the plants. Measurements and numerical values represent averages of typical plant types.

Botanical classification: *Hibiscus syriacus* 'RWOODS11'.

PROPAGATION

Time to initiate roots: 25 days in summer at 18° C. to 27° C.

Time to produce a rooted plant: 45 days in summer at 18° C. to 27° C.

Root description: Dense, freely branching, medium thickness, fibrous. White in color, not accurately measured using The R.H.S. Chart.

PLANT

Plant type: Perennial shrub.

Age of plant described: 3 years old.

Growth habit: Upright and dense.

Plant shape: Elliptic to oblong.

Growth rate: Moderate to high.

Vigor: High.

Height: 65 cm.

Plant spread: 55 cm.

Branching characteristics: Basal; some pinching to encourage well-branched habit.

Primary lateral branches:

*Quantity*.—About 12.

*Length*.—45 cm.

*Diameter*.—5 mm.

*Shape*.—Rounded.

*Strength*.—High.

*Aspect*.—0° to 20° from vertical.

*Color*.—New growth: RHS Yellow-Green 146A. Mature growth: Between RHS Greyed-Green 195A and Greyed-Green 197B. Old growth: Near RHS Grey-Brown 199D.

*Pubescence*.—Slight, on new growth only.

Internode length: 3 cm.

FOLIAGE

Leaf:

*Arrangement*.—Alternate, single.

*Average length*.—8.5 cm.

*Average width*.—6 cm.

*Shape of blade*.—Rhomboidal.

*Apex*.—Acuminate.

*Base*.—Rounded to cuneate.

*Margin*.—Dentate; lobed (3).

*Texture of top surface*.—Glabrous; somewhat coriaceous.

*Texture of bottom surface*.—Glabrous; somewhat coriaceous.

*Aspect*.—Slightly down-curved.

*Color*.—Young foliage upper side: Near RHS Green 137B. Young foliage under side: Near RHS Green 137B. Mature foliage upper side: Near RHS Green NN137A. Mature foliage under side: Near RHS Yellow-Green 147B.

*Venation*.—Type: Palmate. Venation color, upper side: RHS Green 137B. Venation color, under side: RHS Green 137B.

*Petiole*.—Length: 2 cm. Diameter: 2 mm. Color, upper side: RHS Green 137B. Color, under side: RHS Green 137B. Texture, upper side: Slightly pubescent. Texture, under side: Glabrous.

FLOWER

Natural flowering season: Summer (July-August).

Flower arrangement: Flowers borne singly from leaf axils along the lengths of lateral branches, as well as in clusters of 3-5 at the branch apices.

Flower type or form: Whorl.

Flowering habit: From leaf axils along the lengths and at the ends of lateral branches.

Rate of flower opening: 2 to 3 days from bud dehiscence (cracking color) to fully opened flower.

Quantity of flowers per lateral stem: 2 to 5.

Quantity of buds per lateral stem: About 10.

Quantity of flowers and buds per plant: About 150.

Flower longevity on plant: 1 to 2 weeks.

Persistence: Self-cleaning.

Fragrance: None.

Bud:

*Shape*.—Ovate.

*Length*.—1.5 cm.

*Diameter*.—1.2 cm.

*Apex*.—Acute.

*Texture*.—Lightly pubescent.

*Color*: RHS Yellow-Green 147B.

Flower:

*Shape*.—Single whorl.

*Length*.—13 cm.

*Diameter*.—13 cm.

*Depth*.—5 cm.

Petals:

*Quantity*.—5.

*Arrangement*.—Whorl; strongly overlapping, leaving no gaps in between petals.
*Length*.—7 cm.
*Width*.—7 cm.
*Shape*.—Obdeltoid.
*Apex*.—Obtuse.
*Base*.—Cuneate.
*Margin*.—Entire, with some undulation along apex.
*Texture, upper and lower surfaces*.—Soft and silky.
*Color*.—When opening, upper side: RHS Red-Purple 58A at the apex, becoming Red-Purple 64D, with a Red 60A blotch at the base that extends into the venation ⅓ of the way along petal length. When opening, under side: RHS Greyed-Purple 186A at the apex, becoming Red-Purple 186B to 186C at base. Fully opened, upper side: RHS Red-Purple 58A at the apex, becoming Red-Purple 64D, with a Red 60A blotch at the base that extends into the venation ⅓ of the way along petal length. Fully opened, under side: RHS Greyed-Purple 186A at the apex, becoming Red-Purple 186B to 186C at base.

Sepals:
*Quantity*.—5.
*Arrangement*.—Whorl.
*Length*.—1.5 cm.
*Width*.—0.75 cm.
*Shape*.—Triangular.
*Apex*.—Acute.
*Base*.—Fused.
*Margin*.—Entire.
*Color, upper side*.—RHS Yellow-Green 147B.
*Color, under side*.—RHS Yellow-Green 147B.
*Texture, upper side*.—Glabrous.
*Texture, under side*.—Slightly pubescent with short, coarse hairs.

Calyx:
*Length*.—2.5 cm.
*Width*.—3 cm.
*Shape*.—Collar-like.

Peduncle:
*Length*.—2 cm.
*Diameter*.—3 mm.
*Angle*.—45°.
*Strength*.—Moderate.
*Texture*.—Slightly pubescent with short, coarse hairs.
*Color*.—RHS Green 137B.

REPRODUCTIVE ORGANS

Stamens:
*Quantity*.—Around 50, arranged in a staminal column.
*Filament length*.—2 mm.
*Filament color*.—RHS White NN155B.

Anthers:
*Shape*.—Globular.
*Length*.—2 mm.
*Color*.—RHS Greyed-Yellow 162D.
*Pollen*.—Color: RHS Greyed-Yellow 162D. Quantity: Moderate.

Pistil:
*Number*.—5.
*Length*.—5 mm.
*Style*.—Length: 3 mm. Color: RHS White NN155B.
*Stigma*.—Shape: Peltate; hemispherical. Color: RHS White NN155B.

SEEDS 20-40 seeds are borne from dehiscent, five chambered capsules; seeds are a curved, tear-drop shape, with a filamentous or "hairy" coma around the margin.
*Length*.—5 mm.
*Diameter*.—5 mm.
*Color*.—RHS Brown 200C.

OTHER CHARACTERISTICS

Fruit: Not observed.
Disease/pest resistance: Neither resistance nor susceptibility to normal diseases and pests of *Hibiscus syriacus* have been observed.
Temperature tolerance: USDA zones 5 to 9.

What is claimed is:

1. A new and distinct cultivar of *Hibiscus* plant named 'RWOODS11' as herein illustrated and described.

* * * * *